United States Patent
Moriwaki et al.

(10) Patent No.: US 7,547,809 B2
(45) Date of Patent: Jun. 16, 2009

(54) METHOD FOR PRODUCING AROMATIC COMPOUND AND AROMATIC COMPOUND

(75) Inventors: Fumio Moriwaki, Chiba (JP); Hidehiro Matsunami, Chiba (JP); Tetsuya Inoue, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 5 days.

(21) Appl. No.: 11/473,178

(22) Filed: Jun. 23, 2006

(65) Prior Publication Data

US 2007/0060777 A1 Mar. 15, 2007

(30) Foreign Application Priority Data

Sep. 14, 2005 (JP) ............................. 2005-267409

(51) Int. Cl.
*C07C 17/00* (2006.01)
*C07C 15/00* (2006.01)
*H01J 1/62* (2006.01)

(52) U.S. Cl. .................. 570/204; 585/413; 313/505; 313/506

(58) Field of Classification Search ................. 585/413; 313/505, 506; 570/204
See application file for complete search history.

(56) References Cited

U.S. PATENT DOCUMENTS

| | | | |
|---|---|---|---|
| 5,069,894 A * | 12/1991 | Bogdanovic | ............... 423/647 |
| 5,792,557 A | 8/1998 | Nakaya et al. | |
| 6,218,576 B1 | 4/2001 | Shintou et al. | |
| 2004/0007971 A1 | 1/2004 | Higashi et al. | |
| 2008/0113468 A1 | 5/2008 | Spreitzer et al. | |

FOREIGN PATENT DOCUMENTS

| | | |
|---|---|---|
| EP | 1 063 869 A1 | 12/2000 |
| JP | 3-176429 | 7/1991 |
| JP | 8-48656 | 2/1996 |
| JP | 2000-344720 | 12/2000 |
| JP | 2002-175885 | 6/2002 |
| JP | 2003-212799 | 7/2003 |
| JP | 2004-327455 | 11/2004 |
| WO | WO 00/41443 | 7/2000 |
| WO | 2006/037458 | 4/2006 |

OTHER PUBLICATIONS

Tour et al. (abstract of polymeric materials science and engineering (1991).*
Navarro et al (Department of Chemistry, university of New Orleans, Suzuki-Miyarura Cross-Coupling of Sterically hindered Aryl chlorides (2003).*

* cited by examiner

*Primary Examiner*—Jafar Parsa
(74) *Attorney, Agent, or Firm*—Oblon, Spivak, McClelland, Maier & Neustadt, P.C.

(57) ABSTRACT

A process for producing an aromatic compound which can effectively decrease the contents of halogen elements in the aromatic compound and an aromatic compound which is produced in accordance with the process and useful as the material for obtaining an organic electroluminescence device having a long life are provided. The process for producing an aromatic compound comprises bringing an aromatic compound which is produced via an intermediate compound having halogen elements and has contents of halogen elements of 10 to 1,000 ppm by mass into reaction with a dehalogenating agent to decrease the contents of halogen elements to 10 ppm by mass or smaller, and an aromatic compound which is produced in accordance with the process.

9 Claims, No Drawings

METHOD FOR PRODUCING AROMATIC COMPOUND AND AROMATIC COMPOUND

TECHNICAL FIELD

The present invention relates to a process for producing an aromatic compound useful as the organic material for electroluminescence and an aromatic compound obtained in accordance with the process. More particularly, the present invention relates to a process for producing an aromatic compound having decreased contents of halogen elements and an aromatic compound obtained in accordance with the process.

BACKGROUND ART

An organic electroluminescence device (hereinafter, referred to as an organic EL device occasionally) is a light emitting device having at least an organic light emitting layer disposed between a pair of electrodes. The energy generated by recombination of holes injected from the anode and electrons injected from the cathode in the light emitting layer is taken out in the form of light emission.

The organic EL device is a device spontaneously emitting light. The organic EL device has various advantageous properties such as the great current efficiency of light emission, the light weight and the decreased thickness, and many developments have been made recently. As the drawback of the organic EL device, the luminance of the emitted light decreases as the device is driven, and various improvements are attempted to suppress the decrease in the luminance.

For example, it is disclosed that the decrease in the luminance exhibited by an organic EL device can be suppressed by controlling the concentration of halogen impurities in the organic material used for the organic EL device to a value smaller than 1,000 ppm by mass (for example, refer to Patent Reference 1).

As the process for controlling the concentration of halogen impurities in the aromatic compound used for the organic EL device to a desired value, suitable combinations of purification technologies such as purification by sublimation and purification by recrystallization are disclosed in the above patent reference. Recently, a technology for controlling the content of halogen impurities more effectively is required, and it is necessary that a production technology enabling a further decrease in the content of halogen elements in the material for organic EL devices be developed.

In general, the material for organic EL devices is produced in accordance with a process using a halogenated aromatic compound as the intermediate compound such as the Ullman reaction, the Grignard reaction and the Suzuki coupling reaction. It is known that impurities in the used material greatly affect the properties of organic EL devices such as the decrease in the luminance and the initial current efficiency. In general, the increase in the purity is achieved in accordance with a purification process utilizing the difference in the physical properties of the material such as the purification by sublimation, the purification using columns and the purification by recrystallization.

When the attention is focused on the increase in the purity of the material for organic EL devices, it is important that the contents of halogen compounds which are impurities in the material for organic EL devices be decreased and, in particular, the contents of bromine compounds and iodine compounds having great reactivities be decreased. However, the contents of bromine compounds and iodine compounds cannot be decreased sufficiently in accordance with conventional processes.

[Patent Reference 1] Japanese Patent No. 3290432

DISCLOSURE OF THE INVENTION

Problems to be Overcome by the Invention

The present invention has been made under the above circumstances and has an object of providing a process for producing an aromatic compound which can effectively decrease the contents of halogen elements contained in the aromatic compound, and an aromatic compound which is produced in accordance with the process and is useful as the material for obtaining an organic EL device having a long lifetime.

Means for Overcoming the Problems

As the result of intensive studies by the present inventors to overcome the above problem, it was found that an aromatic compound having contents of halogen elements of a specific value or smaller could be obtained by a dehalogenating treatment of a crude product of an aromatic compound having a content of halogen elements in a specific range using a chemical reaction. The present invention has been completed based on the knowledge.

The present invention provides a process for producing an aromatic compound and an aromatic compound obtained in accordance with the process, which are shown in the following:

(1) A process for producing an aromatic compound which comprises bringing an aromatic compound which is produced via an intermediate compound having halogen elements and has contents of halogen elements of 10 to 1,000 ppm by mass into reaction with a dehalogenating agent to decrease the contents of halogen elements to 10 ppm by mass or smaller;

(2) A process for producing an aromatic compound described in (1), wherein the aromatic compound is an organic material for electroluminescence;

(3) A process for producing an aromatic compound described in (1) or (2), wherein the dehalogenating agent is at least one agent selected from Grignard reagents, organolithium compounds and boronic acid derivatives;

(4) A process for producing an aromatic compound described in (1) to (3), wherein the aromatic compound is a compound having a condensed aromatic ring having 14 to 20 ring carbon atoms in a molecule;

(5). A process for producing an aromatic compound described in (1) to (4), wherein the aromatic compound is a compound having 1 to 12 nitrogen atoms in a molecule;

(6) A process for producing an aromatic compound described in (1) to (5), wherein the halogen element is at least one element selected from bromine and iodine;

(7) A process for producing an aromatic compound described in any one of (3) to (6), wherein the Grignard reagent is at least one reagent selected from phenylmagnesium bromide, phenylmagnesium iodide, ethylmagnesium bromide and ethylmagnesium iodide;

(8) A process for producing an aromatic compound described in any one of (3) to (6), wherein the organolithium compound is at least one compound selected from n-butyllithium and phenyllithium;

(9) A process for producing an aromatic compound described in any one of (3) to (6), wherein the boronic acid derivative is phenylboronic acid;

(10) An aromatic compound produced in accordance with the process described in (1) to (9); and

(11) An aromatic compound described in (10), which is an organic material for electroluminescence.

Effects of the Invention

In accordance with the present invention, an aromatic compound having contents of halogen elements of 10 ppm by mass or smaller can be obtained. By using the aromatic compound as the material for an organic EL device, the life of the organic EL device can be increased.

THE MOST PREFERRED EMBODIMENT TO CARRY OUT THE INVENTION

The process for producing an aromatic compound comprises bringing an aromatic compound which is produced via an intermediate compound having halogen elements and has contents of halogen elements of 10 to 1,000 ppm by mass into further reaction with a dehalogenating agent to decrease the contents of halogen elements to 10 ppm by mass or smaller. The above reaction is the treatment of making aromatic halogen compounds as the impurities in the aromatic compound obtained by the synthesis harmless by converting the aromatic halogen compounds into other compounds.

As the process for converting aromatic halogen compounds into other compounds, conventional reactions using a dehalogenating agent can be used. Grignard reactions, reactions using organolithium compounds and reactions using boronic acid derivatives (Suzuki coupling reactions) are preferable due to the great yield of the reaction.

The Grignard reaction is a coupling reaction between an aromatic halogen compound and a Grignard reagent. As the Grignard reagent, a commercial reagent or an arylmagnesium bromide, an arylmagnesium iodide, an alkylmagnesium bromide or an alkylmagnesium iodide which is suitably prepared can be used. Among the above reagents, phenyl-magnesium bromide, phenylmagnesium iodide, ethylmagnesium bromide and ethylmagnesium iodide are preferable. Phenylmagnesium bromide and phenylmagnesium iodide are more preferable. The Grignard reagent may be used singly or in combination of two or more.

As the solvent for the reaction, a conventional solvent can be used. Specifically, ether-based solvents such as dimethoxyethane and tetrahydrofuran are preferable. A mixed solvent of these solvents may be used. It is desirable that the solvent for the reaction is treated for dehydration in advance.

The temperature of the reaction is selected, in general, in the range of −30 to 100° C. and preferably in the range of −10 to 80° C. The time of the reaction is selected, in general, in the range of 1 to 48 hours and preferably in the range of 2 to 8 hours. It is preferable that the reaction in conducted under a stream of argon.

The reaction using an organolithium (Li) compound is, specifically, a coupling reaction between an aromatic halogen compound and an organolithium reagent. As the organolithium compound, various commercial reagents can be used. Aryllithiums and alkyllithiums are preferable. n-Butyllithium and phenyllithium are more preferable. The organolithium compound may be used singly or in combination of two or more.

As the solvent for the reaction, a conventional solvent can be used. Cyclic hydrocarbon-based solvents such as cyclohexane and decaline and ether-based solvents such as dimethoxyethane and tetrahydrofuran are preferable. A mixed solvent of these solvents may be used.

The temperature of the reaction is selected, in general, in the range of −100 to 50° C. and preferably in the range of −80 to 10° C. The time of the reaction is selected, in general, in the range of 1 to 48 hours and preferably in the range of 1 to 8 hours. It is preferable that the reaction is conducted under a stream of nitrogen or argon.

The reaction using a boronic acid derivative is also called the Suzuki coupling reaction and is a coupling reaction between an aromatic halogen compound and a boronic acid derivative. As the boronic acid derivative, various commercial boronic acid derivatives can be used. Phenylboronic acid and derivatives thereof are preferable. The boronic acid derivative may be used singly or in combination of two or more.

The Suzuki coupling reaction is preferable since the reactivity with halogens is great and, moreover, in the dehalogenation treatment of a material having a substituent such as nitro group and methoxy group, no reactions take place with the substituent.

As the solvent for the reaction, a conventional solvent can be used. Examples of the solvent include aromatic hydrocarbon-based solvents such as toluene and xylene, cyclic hydrocarbon-based solvents such as cyclohexane and decaline and ether-based solvents such as dimethoxyethane and tetrahydrofuran. Among these solvents, aromatic hydrocarbon-based solvents such as toluene and xylene and ether-based solvents such as dimethoxyethane and tetrahydrofuran are preferable. A mixed solvent of these solvents may be used.

It is preferable that the reaction is conducted in the condition of suspension while a solvent comprising the above solvent and water and forming two layers is stirred. In general, a base is used in this reaction. Examples of the base include carbonates, phosphates and hydroxides of alkali metals and alkaline earth metals. Potassium carbonate, cesium carbonate and potassium phosphate are preferable.

In this reaction, in general, a complex compound of a transition metal such as Pd and Ni can be used as the catalyst. Specifically, $Pd(PPh_3)_4$ and palladium acetate are preferable. A complex compound of a transition metal such as Pd and Ni may be used in combination with a phosphorus-based ligand. As the ligand, tris(o-tolyl)phosphine and tri(t-butyl)phosphine are preferable.

The temperature of the reaction is selected, in general, in the range of 50 to 200° C. and preferably in the range of 70 to 150° C. The time of the reaction is selected, in general, in the range of 4 to 48 hours and preferably in the range of 8 to 16 hours. It is preferable that the reaction is conducted under the stream of nitrogen or argon.

In the production of the aromatic compound, the contents of halogen elements in the aromatic compound can be remarkably decreased by the treatment using the chemical reaction described above when the aromatic compound is treated in the stage of a crude product containing at most 1,000 ppm by mass of halogen elements.

When the above crude product is purified in accordance with a conventional process to decrease the contents of halogen elements in the aromatic compound to 100 ppm by mass or smaller, the concentrations of halogen impurities can be further decreased by the above treatment using the chemical reaction described above.

The contents of halogen elements in the aromatic compound can be decreased to 10 ppm by mass or smaller by the above dehalogenation treatment. It is preferable that the contents are decreased to 1 ppm by mass or smaller.

The process of the present invention can be effectively applied to production of any aromatic compounds. In particular, the process is advantageously applied to the production of the material for organic EL devices using a crude product of an aromatic compound having a condensed aromatic ring having 14 to 20 ring carbon atoms in the molecule. Examples of the aromatic compound having a condensed aromatic ring having 14 to 20 ring carbon atoms in the molecule include anthracene, phenanthrene, pyrene, chrysene, benzanthracene, perylene, fluoranthene and tetracene.

As the aromatic compound having a condensed aromatic ring in the molecule, for example, compounds shown in 1 to 7 in the following are preferable.

1. Anthracene Derivatives Represented by the Following General Formula (1):

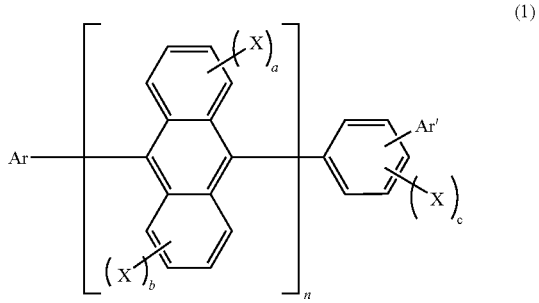

In general formula (1), Ar represents a substituted or unsubstituted condensed aromatic group having 10 to 50 ring carbon atoms. Examples of the condensed aromatic group include 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 3-methyl-2-naphthyl group and 4-methyl-1-anthryl group. As the condensed aromatic group represented by Ar, a group selected from groups represented by the following formulae is preferable.

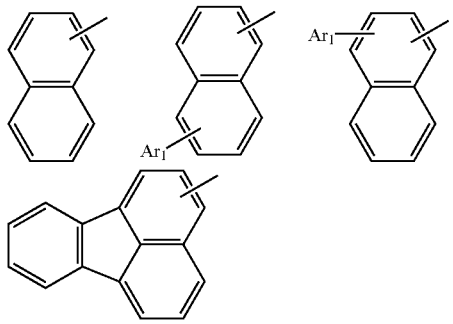

In the above formulae, $Ar_1$ represents a substituted or unsubstituted aromatic group having 6 to 50 ring carbon atoms.

Examples of the group represented by $Ar_1$ include phenyl group, 1-naphthyl group, 2-naphthyl group, 1-anthryl group, 2-anthryl group, 9-anthryl group, 9-(10-phenyl)anthryl group, 9-(10-naphthyl-1-yl)anthryl group, 9-(10-naphthyl-2-yl)anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, 3-methyl-2-naphthyl group, 4-methyl-1-naphthyl group and 4-methyl-1-anthryl group.

Among these groups, phenyl group, 1-naphthyl group, 2-naphthyl group, 9-(10-phenyl)anthryl group, 9-(10-naphthyl-1-yl)anthryl group, 9-(10-naphthyl-2-yl)anthryl group, 9-phenanthryl group, 1-pyrenyl group, 2-pyrenyl group, 4-pyrenyl group, 2-biphenylyl group, 3-biphenylyl group, 4-biphenylyl group, o-tolyl group, m-tolyl group, p-tolyl group and p-t-butylphenyl group are preferable.

The above aromatic groups may be substituted with substituents. Examples of the substituent include alkyl groups (such as methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, cyclopropyl group, cyclobutyl group, cyclopentyl group, cyclohexyl group, 4-methylcyclohexyl group, 1-adamantyl group, 2-adamantyl group, 1-norbornyl group and 2-norbornyl group), alkoxyl groups having 1 to 6 carbon atoms (such as ethoxyl group, methoxyl group, i-propoxyl group, n-propoxyl group, s-butoxyl group, t-butoxyl group, pentoxyl group, hexyloxyl group, cyclopentoxyl group and cyclohexyloxyl group), aryl groups having 5 to 40 ring atoms, amino groups substituted with aryl groups having 5 to 40 ring atoms, ester groups having aryl groups having 5 to 40 ring atoms, ester groups having alkyl groups having 1 to 6 carbon atoms, cyano group, nitro group and halogen atoms.

Ar' represents a substituted or unsubstituted aromatic group having 6 to 50 ring carbon atoms. Examples of the aromatic group include the groups shown above as the examples of the group represented by $Ar_1$. As the aromatic group, the groups shown as the preferable groups among the groups represented by $Ar_1$ are preferable.

In general formula (1), X represents a substituted or unsubstituted aromatic group having 6 to 50 ring carbon atoms, a substituted or unsubstituted aromatic heterocyclic group having 5 to 50 ring carbon atoms, a substituted or unsubstituted alkyl groups having 1 to 50 carbon atoms, a substituted or unsubstituted cycloalkyl groups, a substituted or unsubstituted alkoxyl group having 1 to 50 carbon atoms, a substituted or unsubstituted aralkyl group having 6 to 60 carbon atoms, a substituted or unsubstituted aryloxyl group having 5 to 50 ring carbon atoms, a substituted or unsubstituted arylthio group having 5 to 50 ring carbon atoms, a substituted or unsubstituted alkoxycarbonyl group having 1 to 50 carbon atoms, carboxyl group, halogen atoms, cyano group, nitro group or hydroxyl group.

Examples of the substituted or unsubstituted aromatic group having 6 to 50 ring carbon atoms represented by X include the groups shown above as the examples of the aromatic group represented by $Ar_1$.

Examples of the substituted or unsubstituted aromatic heterocyclic group having 5 to 50 ring carbon atoms include 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methyl-pyrrol-5-yl group, 3-methylpyrrol-1-yl group, 3-methyl-pyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group.

Examples of the substituted or unsubstituted alkyl group represented by X include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloro-propyl group, bromomethyl group, 1-bromoethyl group, 2-bromoethyl group, 2-bromoisobutyl group, 1,2-dibromoethyl group, 1,3-dibromo-isopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triamino-propyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group.

Examples of the substituted or unsubstituted cycloalkyl group include cyclopropyl group, cyclobutyl group, cyclopentyl group, cyclohexyl group, 4-methylcyclohexyl group, 1-adamantyl group, 2-adamantyl group, 1-norbornyl group and 2-norbornyl group.

The substituted or unsubstituted alkoxyl group is a group represented by —OY. Examples of the group represented by Y include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromo-isopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triamino-propyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group.

Examples of the substituted or unsubstituted aralkyl group include benzyl group, 1-phenylethyl group, 2-phenylethyl group, 1-phenyl-isopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group.

The substituted or unsubstituted aryloxyl group is represented by —OY'. Examples of the group represented by Y' include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 2-pyrrolyl group, 3-pyrrolyl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group,
1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methyl-pyrrol-5-yl group, 3-methylpyrrol-1-yl group, 3-methyl-pyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group.

The substituted or unsubstituted arylthio group is a group represented by —SY". Examples of the group represented by Y" include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 2-pyrrolyl group, 3-pyrrolyl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 6-quinoxanyl group, 6-quinoxanyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin 1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methyl-pyrrol-5-yl group, 3-methylpyrrol-1-yl group, 3-methyl-pyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group.

The substituted or unsubstituted alkoxycarbonyl group is represented by —COOZ. Examples of the group represented by Z include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloro-propyl group, bromomethyl group, 1-bromoethyl group, 2-bromoethyl group, 2-bromoisobutyl group, 1,2-dibromoethyl group, 1,3-dibromo-isopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triamino-propyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitro-ethyl group, 1,3-dinitroisopropyl group, 2,3-dinitro-t-butyl group, 1,2,3-trinitropropyl group.

Examples of the divalent group forming the ring include tetramethylene group, pentamethylene group, hexamethylene group, diphenylmethane-2,2'-diyl group, diphenylethane-3,3'-diyl group and diphenylpropane-4,4'-diyl group.

Examples of the halogen atom include fluorine atom, chlorine atom, bromine atom and iodine atom.

In general formula (1), a, b and c each represent an integer of 0 to 4 and preferably 0 or 1. n represents an integer of 1 to 3. When n represents 2 or 3, the plurality of groups in [ ] shown in the following:

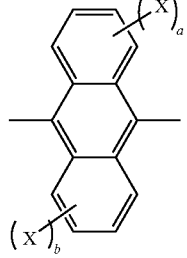

may be the same with or different from each other.

2. Asymmetric Monoanthracene Derivative Represented by the Following General Formula (2):

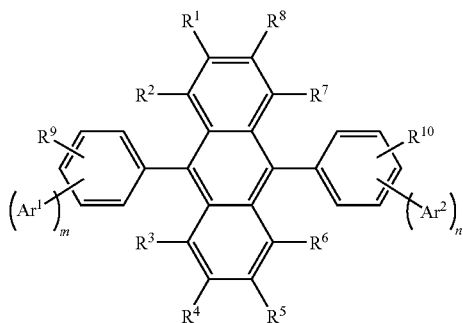

(2)

In general formula (2), m and n each represent an integer of 1 to 4 and preferably 1 or 2.

When m=n=1 and the positions of bonding of the groups represented by $Ar^1$ and $Ar^2$ to the respective benzene rings are horizontally symmetrical, $Ar^1$ and $Ar^2$ do not represent the same group. When m or n represents an integer of 2 to 4, m and n represent integers different from each other. In the present invention, when the groups represented by $Ar^1$ and $R^9$ are bonded at positions $X^1$ and $X^2$, respectively, of the benzene ring bonded to the 9-position of the anthracene ring, and the groups represented by $Ar^2$ and $R^{10}$ are bonded at positions $X^1$ and $X^2$, respectively, of the benzene ring bonded to the 10-position of the anthracene ring, the positions of bonding of the groups are defined as horizontally symmetrical.

In other words, in the anthracene derivative represented by general formula (2), benzene rings each substituted with an aromatic group and bonded to the anthracene nucleus have a horizontally asymmetric structure and, therefore, the above anthracene derivative has an asymmetric structure.

When the substituents bonded to the 9-position and the 10-position of the anthracene nucleus are the same with each other, this structure is not included in the asymmetric structure defined above even when the substituents at the 2-position and the 3-positions of the anthracene nucleus are different from each other.

In general formula (2) shown above, it is preferable that m and/or n represents 1. When m=1, compounds represented by the following general formulae (3) to (5) are more preferable.

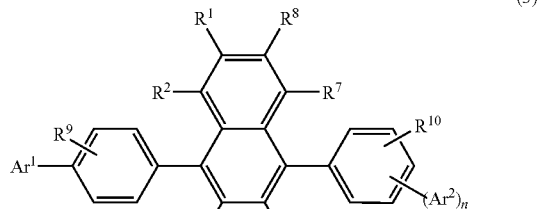

(3)

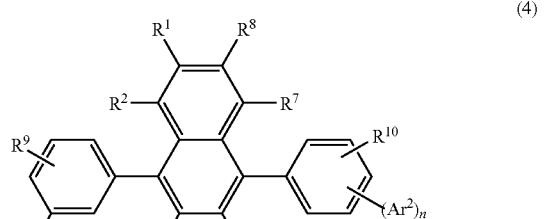

(4)

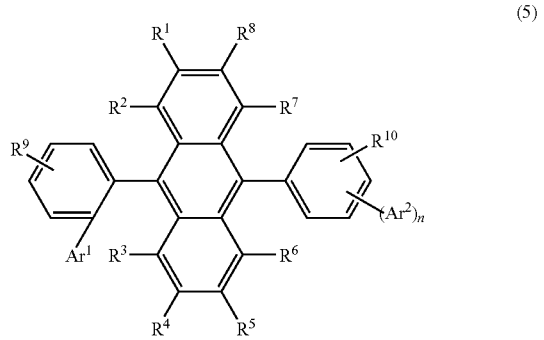

(5)

In general formulae (3) to (5), $Ar^1$, $Ar^2$, n and $R^1$ to $R^{10}$ are as defined for general formula (2) in the above. Similarly to the case described above, $Ar^1$ and $Ar^2$ do not represent the same group when n=1 and the positions of bonding of the groups represented by $Ar^1$ and $Ar^2$ are horizontally symmetrical.

In general formula (2), $Ar^1$ and $Ar^2$ each independently represent a substituted or unsubstituted aromatic cyclic group having 6 to 50 ring carbon atoms.

Examples of the substituted or unsubstituted aromatic cyclic group having 6 to 50 ring carbon atoms represented by $Ar^1$ and $Ar^2$ include the groups shown above as the examples of the corresponding group in general formula (1). Phenyl group, 1-naphthyl group, 2-naphthyl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, o-tolyl group, m-tolyl group, p-tolyl group and p-t-butylphenyl group are preferable.

In general formula (2), $R^1$ to $R^{10}$ each independently represent hydrogen atom, a substituted or unsubstituted aromatic cyclic group having 6 to 50 ring carbon atoms, a substituted or unsubstituted aromatic heterocyclic group having 5 to 50 ring carbon atoms, a substituted or unsubstituted alkyl group having 1 to 50 carbon atoms, a substituted or unsubstituted cycloalkyl group, a substituted or unsubstituted alkoxyl group having 1 to 50 carbon atoms, a substituted or unsubstituted aralkyl group having 6 to 50 carbon atoms, a substituted or unsubstituted aryloxyl group having 5 to 50 ring carbon atoms, a substituted or unsubstituted arylthio group having 5 to 50 ring carbon atoms, a substituted or unsubstituted alkoxycarbonyl group having 1 to 50 carbon atoms, a substituted or unsubstituted silyl group, carboxyl group, a halogen atom, cyano group, nitro group or hydroxyl group.

Examples of the substituted or unsubstituted aromatic cyclic group, the substituted or unsubstituted aromatic heterocyclic group, the substituted or unsubstituted alkyl group, the substituted or unsubstituted cycloalkyl group, the substituted or unsubstituted alkoxyl group, the substituted or unsubstituted aralkyl group, the substituted or unsubstituted aryloxyl group, the substituted or unsubstituted arylthio group and the substituted or unsubstituted alkoxycarbonyl group represented by $R^1$ to $R^{10}$ include the groups shown as the examples of the corresponding groups represented by X in general formula (1).

Examples of the halogen atom represented by $R^1$ to $R^{10}$ include fluorine atom, chlorine atom, bromine atom and iodine atom.

Examples of the substituent to the above groups represented by $Ar^1$, $Ar^2$ and $R^1$ to $R^{10}$ include halogen atoms, hydroxyl group, nitro group, cyano group, alkyl groups, aryl groups, cycloalkyl groups, alkoxyl groups, aromatic heterocyclic groups, aralkyl groups, aryloxyl groups, arylthio groups, alkoxycarbonyl groups and carboxyl group.

3. Asymmetric Anthracene Derivatives Represented by the Following General Formula (6):

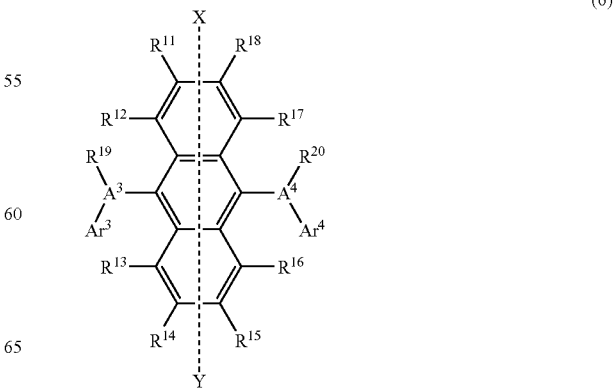

(6)

As the asymmetric anthracene derivative represented by general formula (6), the case in which groups are bonded to the 9-position and the 10-position of anthracene symmetrically with respect to the X-Y axis of the anthracene shown above is excluded. That the case in which groups are bonded symmetrically with respect to the X-Y axis is excluded preferably means that general formula (6) has the following structures:

(I) $A^3$ and $A^4$ are different from each other.
(II) When $A^3$ and $A^4$ are the same with each other,
  (II-i) $Ar^3$ and $Ar^4$ are different from each other.
  (II-ii) $R^{19}$ and $R^{20}$ are different from each other.
  (II-iii) When $Ar^3$ and $Ar^4$ are the same with each other, and $R^{19}$ and $R^{20}$ are the same with each other,
    (II-iii-1) The position of bonding of $A^3$ to the 9-position of anthracene is different from the position of bonding of $A^4$ to the 10-position of anthracene.
    (II-iii-2) When neither $Ar^3$ nor $Ar^4$ represents hydrogen atom, the position of bonding of $Ar^3$ in $A^3$ is different from the position of bonding of $Ar^4$ in $A^4$.
    (II-iii-3) When neither of $R^{19}$ nor $R^{20}$ represents hydrogen atom, the position of bonding of $R^{19}$ in $A^3$ is different form the position of bonding of $R^{20}$ in $A^4$.

In general formula (6), $A^3$ and $A^4$ each independently represent a substituted or unsubstituted condensed aromatic cyclic group having 10 to 20 ring carbon atoms and preferably 10 to 16 ring carbon atoms.

Examples of the substituted or unsubstituted condensed aromatic cyclic represented by $A^3$ and $A^4$ include 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 3-methyl-2-naphthyl group, 4-methyl-1-naphthyl group and 4-methyl-1-anthryl group.

Among these groups, 1-naphthyl group, 2-naphthyl group and 9-phenanthryl group are preferable.

In general formula (6), $Ar^3$ and $Ar^4$ each independently represent hydrogen atom or a substituted or unsubstituted aromatic cyclic group having 6 to 50 ring carbon atoms and preferably 6 to 16 ring carbon atoms.

Examples of the substituted or unsubstituted aromatic cyclic group represented by $Ar^3$ and $Ar^4$ include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl 10 group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group and 4'-t-butyl-p-terphenyl-4-yl group.

Among these groups, phenyl group, 1-naphthyl group, 2-naphthyl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, o-tolyl group, m-tolyl group, p-tolyl group and p-t-butylphenyl group are preferable.

In general formula (6), $R^{11}$ to $R^{20}$ each independently represent hydrogen atom, a substituted or unsubstituted aromatic group having 6 to 50 ring carbon atoms, a substituted or unsubstituted aromatic heterocyclic group having 5 to 50 ring carbon atoms, a substituted or unsubstituted alkyl groups having 1 to 50 carbon atoms, a substituted or unsubstituted cycloalkyl groups, a substituted or unsubstituted alkoxyl group having 1 to 50 carbon atoms, a substituted or unsubstituted aralkyl group having 6 to 50 carbon atoms, a substituted or unsubstituted aryloxyl group having 5 to 50 ring carbon atoms, a substituted or unsubstituted arylthio group having 5 to 50 ring carbon atoms, a substituted or unsubstituted alkoxycarbonyl group having 1 to 50 carbon atoms, a substituted or unsubstituted silyl group, carboxyl group, halogen atoms, cyano group, nitro group or hydroxyl group.

Examples of the substituted or unsubstituted aromatic cyclic group, the substituted or unsubstituted aromatic heterocyclic group, the substituted or unsubstituted alkyl group, the substituted or unsubstituted cycloalkyl group, the substituted or unsubstituted alkoxyl group, the substituted or unsubstituted aralkyl group, the substituted or unsubstituted aryloxyl group, the substituted or unsubstituted arylthio group and the substituted or unsubstituted alkoxycarbonyl group represented by $R^{11}$ to $R^{20}$ include the groups shown as the examples of the corresponding groups represented by X in general formula (1).

Examples of the halogen atom represented by $R^{11}$ to $R^{20}$ include fluorine atom, chlorine atom, bromine atom and iodine atom.

Examples of the substituent to the above groups represented by $Ar^3$, $Ar^4$ and $R^{11}$ to $R^{20}$ include halogen atoms, hydroxyl group, nitro group, cyano group, alkyl groups, aryl groups, cycloalkyl groups, alkoxyl groups, aromatic heterocyclic groups, aralkyl groups, aryloxyl groups, arylthio groups, alkoxycarbonyl groups and carboxyl group.

$Ar^3$, $Ar^4$ and $R^{11}$ to $R^{20}$ may each represent a plurality of atoms or groups. Groups adjacent to each other may form a saturated or unsaturated cyclic structure. Examples of the cyclic structure include unsaturated six-membered rings such as benzene ring and saturated and unsaturated five-membered and seven-membered cyclic structures.

In the present invention, it is preferable that the asymmetric anthracene derivative represented by general formula (6) has a naphthalen-1-yl group having a substituent at the 4-position and/or a substituted or unsubstituted condensed aromatic cyclic group having 12 to 20 ring carbon atoms. Examples of the substituent include the substituents shown above as the examples of the substituent to the groups represented by $Ar^3$, $Ar^4$ and $R^1$ to $R^{20}$.

4. An Asymmetric Anthracene Derivative Represented by the Following General Formula (6'):

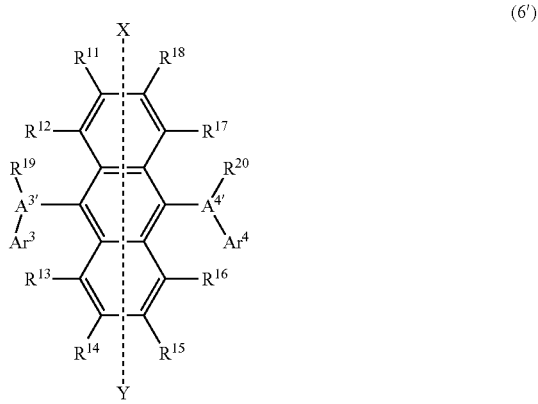

(6')

General formula (6') is the formula obtained by restricting general formula (6) in a manner such that $A^{3'}$ and $A^{4'}$ each independently represent a substituted or unsubstituted condensed aromatic cyclic group having 10 to 20 ring carbon atoms, and at least one of $A^{3'}$ and $A^{4'}$ represents naphthalen-1-yl group having a substituent at the 4-position or a substituted or unsubstituted condensed aromatic cyclic group having 12 to 20 ring carbon atoms. Since $Ar^3$, $Ar^4$ and $R^{11}$ to $R^{20}$ each independently represent the same atom or group as that in general formula (6), examples of the atoms, the groups, the preferable groups and the substituents include the atoms, the groups, the preferable groups and the substituents shown as the corresponding examples in general formula (6). Similarly to general formula (6), the case in which groups are bonded to the 9-position and the 10-position of anthracene symmetrically with respect to the X-Y axis of the anthracene shown above is excluded in general formula (6').

5. Asymmetric Pyrene Derivatives Represented by the Following General Formula (7):

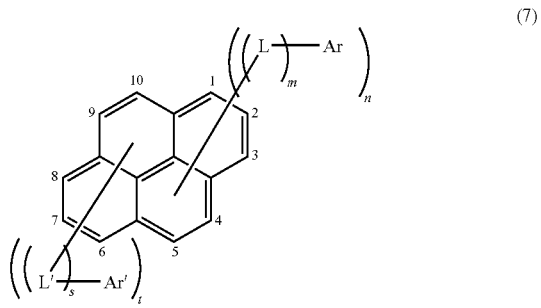

(7)

In general formula (7), Ar and Ar' each represents a substituted or unsubstituted aromatic group having 6 to 50 ring carbon atoms.

Examples of the aromatic group include phenyl group, 1-naphthyl group, 2-naphthyl group, 1-anthryl group, 2-anthryl group, 9-anthryl group, 9-(10-phenyl)anthryl group, 9-(10-naphthyl-1-yl)anthryl group, 9-(10-naphthyl-2-yl)anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, 3-methyl-2-naphthyl group, 4-methyl-1-naphthyl group and 4-methyl-1-anthryl group.

Among these groups, phenyl group, 1-naphthyl group, 2-naphthyl group, 9-(10-phenyl)anthryl group, 9-(10-naphthyl-1-yl)anthryl group, 9-(10-naphthyl-2-yl)anthryl group, 9-phenanthryl group, 1-pyrenyl group, 2-pyrenyl group, 4-pyrenyl group, 2-biphenylyl group, 3-biphenylyl group, 4-biphenylyl group, o-tolyl group, m-tolyl group, p-tolyl group and p-t-butylphenyl group are preferable.

The above aromatic groups may be substituted with substituents. Examples of the substituent include alkyl groups (such as methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, cyclopropyl group, cyclobutyl group, cyclopentyl group, cyclohexyl group, 4-methylcyclohexyl group, 1-adamantyl group, 2-adamantyl group, 1-norbornyl group and 2-norbornyl group), alkoxyl groups having 1 to 6 carbon atoms (such as ethoxyl group, methoxyl group, i-propoxyl group, n-propoxyl group, s-butoxyl group, t-butoxyl group, pentoxyl group, hexyloxyl group, cyclopentoxyl group and cyclohexyloxyl group), aryl groups having 5 to 40 ring atoms, amino groups substituted with aryl groups having 5 to 40 ring atoms, ester groups having aryl groups having 5 to 40 ring atoms, ester groups having alkyl groups having 1 to 6 carbon atoms, cyano group, nitro group and halogen atoms.

In general formula (7), L and L' each represent a substituted or unsubstituted phenylene group, a substituted or unsubstituted naphthalenylene group, a substituted or unsubstituted fluorenylene group, a substituted or unsubstituted dibenzosilolylene group. Substituted and unsubstituted phenylene groups and substituted and unsubstituted fluorenylene groups are preferable.

Examples of the substituent include the substituents shown above as the examples of the substituent to the aromatic group.

In general formula (7), m represents an integer of 0 to 2 and preferably 0 or 1, n represents an integer of 1 to 4 and preferably 1 or 2, s represents an integer of 0 to 2 and preferably 0 or 1, and t represents an integer of 0 to 4 and preferably 0 to 2.

In general formula (7), the group represented by L or Ar is bonded to one of the 1- to 5-positions of pyrene. The group represented by L' or Ar' is bonded to one of the 6- to 10-positions of pyrene.

In general formula (7), when n+t represent an even number, the groups represented by Ar, Ar', L and L' satisfy the following condition (1) or (2):
(1) Ar≠Ar' and/or L≠L' (≠ means that the groups have different structures).
(2) When Ar=Ar' and L=L',
    (2-1) m≠s and/or n≠t, or
    (2-2) when m=s and n=t,
        (2-2-1) L and L' or pyrene is bonded to different positions on Ar and Ar', respectively.
        (2-2-2) when L and L' or pyrene is bonded to the same position on Ar and Ar', the case in which the positions of substitution of L and L' or Ar and Ar' on pyrene are the 1- and 6-positions or the 2- and 7-positions is excluded.

In general formula (7), Ar and Ar' each represent a substituted or unsubstituted aromatic group having 6 to 50 ring carbon atoms, and L and L' each represent a substituted or unsubstituted phenylene group, a substituted or unsubstituted naphthalenylene group, a substituted or unsubstituted fluorenylene group, a substituted or unsubstituted dibenzosilolylene group.

m represents an integer of 0 to 2, n represents an integer of 1 to 4, s represents an integer of 0 to 2 1, and t represents an integer of 0 to 4. The group represented by L or Ar is bonded to one of the 1- to 5-positions of pyrene. The group represented by L' or Ar' is bonded to one of the 6- to 10-positions of pyrene.

When n+t represent an even number, the groups represented by Ar, Ar', L and L' satisfy the following condition (1) or (2):

(1) Ar≠Ar' and/or L≠L' (≠ means that the groups have different structures).
(2) When Ar=Ar and L=L',
  (2-1) m≠s and/or n≠t, or
  (2-2) when m=s and n=t,
    (2-2-1) L and L' or pyrene is bonded to different positions on Ar and Ar', respectively.
    (2-2-2) when L and L' or pyrene is bonded to the same position on Ar and Ar', the case in which the positions of substitution of L and L' or Ar and Ar' on pyrene are the 1- and 6-positions or the 2- and 7-positions is excluded.

6. Asymmetric Pyrene Derivative Represented by the Following General Formula (8):

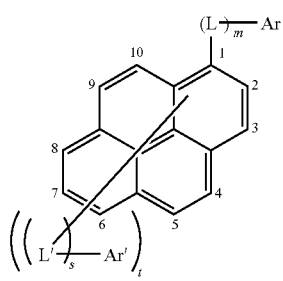

(8)

In general formula (8), Ar, Ar', L, L', m, s and t are as defined for general formula (7). Examples of the groups represented by Ar, Ar', L and L' and examples of the substituents are as shown for general formula (7). In general formula (8), the group represented by L' or Ar' is bonded to one of the 2- to 10-positions of pyrene.

In general formula (8), when t represents an odd number, Ar, Ar', L and L' satisfy the following condition (1') or (2'):

(1') Ar≠Ar' and/or L≠L' (≠ means that the groups have different structures).
(2') When Ar=Ar' and L=L',
  (2-1') m=s and/or t*1, or
  (2-2') when m=s and t=1,
    (2-2-1) L and L' or pyrene is bonded to different positions on Ar and Ar', respectively.
    (2-2-2) when L and L' or pyrene is bonded to the same position on Ar and Ar', the case in which the position of substitution of L' or Ar' on pyrene is the 6-position is excluded.

7. Asymmetric Pyrene Derivative Represented by the Following General Formula (9):

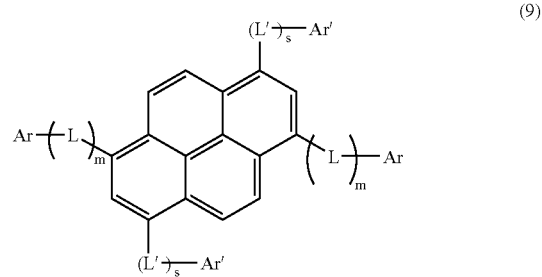

In general formula (9), Ar, Ar', L, L', m and s are as defined for general formula (7). Examples of the groups represented by Ar, Ar', L and L', preferable examples of the groups represented by Ar, Ar', L and L' and examples of the substituents are as shown for general formula (7).

The process of the present invention can be advantageously applied to production of a material for organic EL devices using a crude product of an aromatic compound having 1 to 12 nitrogen atoms in the molecule.

Examples of the aromatic compound having 1 to 12 nitrogen atoms include amine-based compounds such as aromatic diamines, aromatic triamines and aromatic tetraamines; carbazole-based compounds such as dicarbazole derivatives, tricarbazole derivatives and tetracarbazole derivatives; benzimidazole-based compounds; phenanthroline-based compounds; quinoxaine-based compounds; hexaazatriphenylene-based compounds; indolidine-based compounds; bipyridyl-based compounds; pyrimidine-based compounds; triazine-based compounds; and phthalocyanine-based compounds.

Among the aromatic compounds described above, compounds having a low symmetry have a tendency that halogen impurities are left remaining in the material for organic EL devices since many types of aromatic halogenated compounds are used and complicated reactions are conducted utilizing the difference in reactivity of halogen atoms. Compounds having nitrogen atom in the molecule tend to form an intramolecular complex with an isolated halogen, and halogen impurities tend to be left remaining in the molecule. Due to these reasons, the process comprising the treatment using chemical reaction such as the process of the present invention is very effective for decreasing the contents of halogens in the material for organic EL devices in the high purity region.

Examples of the aromatic compound having 1 to 12 nitrogen atoms in the molecule include the compounds represented by the following general formulae (10) to (14):

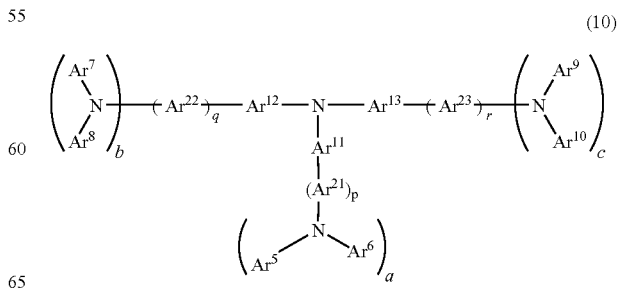

(10)

In general formula (10), $Ar^5$ to $Ar^{13}$ and $Ar^{21}$ to $Ar^{23}$ each independently represent a group selected from substituted and unsubstituted aromatic groups having 6 to 50 ring carbon atoms and aromatic heterocyclic groups having 5 to 50 ring carbon atoms. The pair of groups represented by $Ar^5$ and $Ar^6$, $Ar^7$ and $Ar^8$ or $Ar^9$ and $Ar^{10}$ may be bonded to each other to form a saturated or unsaturated ring. a to c and p to r each represent an integer of 0 to 3. Examples of the substituted or unsubstituted aromatic group having 6 to 50 ring carbon atoms include the groups shown as the examples of the corresponding group in general formula (7). Examples of the aromatic heterocyclic group having 5 to 50 ring carbon atoms include the groups shown as the examples of the group represented by X in general formula (1).

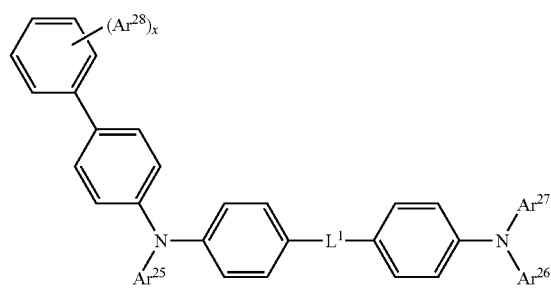

(11)

In general formula (11), $Ar^{25}$ to $Ar^{28}$ each independently represent a group selected from substituted and unsubstituted aromatic groups having 6 to 50 ring carbon atoms and substituted and unsubstituted aromatic heterocyclic groups having 5 to 50 ring carbon atoms. The groups represented by $Ar^{26}$ and $Ar^{27}$ may be bonded to each other to form a saturated or unsaturated ring. $L^1$ represents the single bond or a group selected from substituted and unsubstituted aromatic group 6 to 50 ring carbon atoms and substituted and unsubstituted aromatic heterocyclic groups having 5 to 50 ring carbon atoms. x represents an integer of 0 to 5. Examples of the substituted or unsubstituted aromatic group having 6 to 50 ring carbon atoms and aromatic heterocyclic group having 5 to 50 ring carbon atoms include the groups described above for general formula (10).

$$HAr-L^2-Ar^{31}-Ar^{32} \quad (12)$$

In general formula (12), HAr represents a substituted or unsubstituted heterocyclic group having 3 to 40 carbon atoms and nitrogen atom, $L^2$ represents the single bond or a group selected from substituted and unsubstituted arylene groups having 6 to 60 carbon atoms, substituted and unsubstituted heteroarylene groups having 3 to 60 carbon atoms and substituted or unsubstituted fluorenylene groups, $Ar^{31}$ represents a substituted or unsubstituted divalent aromatic hydrocarbon group having 6 to 60 carbon atoms, and $Ar^{32}$ represents a group selected from substituted and unsubstituted aryl groups having 6 to 60 carbon atoms and substituted and unsubstituted heteroaryl groups having 3 to 60 carbon atoms.

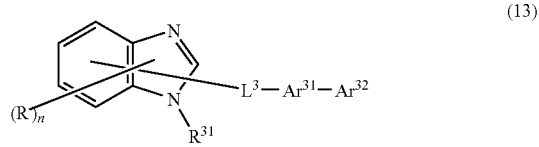

(13)

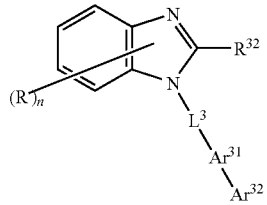

(14)

In general formulae (13) and (14), R represents hydrogen atom or a group selected from substituted and unsubstituted aryl groups having 6 to 60 carbon atoms, substituted and unsubstituted pyridyl group, substituted and unsubstituted quinolyl group, substituted and unsubstituted alkyl groups having 1 to 20 carbon atoms and substituted and unsubstituted alkoxyl groups having 1 to 20 carbon atoms. n represents an integer of 0 to 4. $R^{31}$ represents a group selected from substituted and unsubstituted aryl groups having 6 to 60 carbon atoms, substituted and unsubstituted pyridyl group, substituted and unsubstituted quinolyl group, substituted and unsubstituted alkyl groups having 1 to 20 carbon atoms and substituted and unsubstituted alkoxyl groups having 1 to 20 carbon atoms. $R^{32}$ represents hydrogen atom or a group selected from substituted and unsubstituted aryl groups having 6 to 60 carbon atoms, substituted and unsubstituted pyridyl group, substituted and unsubstituted quinolyl group, substituted and unsubstituted alkyl groups having 1 to 20 carbon atoms and substituted and unsubstituted alkoxyl groups having 1 to 20 carbon atoms. $L^3$ represents a group selected from substituted and unsubstituted arylene groups having 6 to 60 carbon atoms, substituted and unsubstituted pyridinylene groups, substituted and unsubstituted quinolynylene groups and substituted and unsubstituted fluorenylene groups. $Ar^{31}$ represents a group selected from substituted and unsubstituted arylene group having 6 to 60 carbon atoms, substituted and unsubstituted pyridinylene groups and substituted and unsubstituted quinolynylene groups. $Ar^{32}$ represents a group selected from substituted and unsubstituted aryl groups having 6 to 60 carbon atoms, substituted and unsubstituted pyridyl group, substituted and unsubstituted quinolyl group, substituted and unsubstituted alkyl groups having 1 to 20 carbon atoms and substituted and unsubstituted alkoxyl groups having 1 to 20 carbon atoms.

The aromatic compound of the present invention is advantageously used as the material for organic EL devices, organic semiconductors and electronic photosensitive materials. Typical examples of the construction of the organic EL device using the aromatic compound of the present invention include:

(1) An anode/a light emitting layer/a cathode;
(2) An anode/a hole injecting layer/a light emitting layer/a cathode;
(3) An anode/a light emitting layer/an electron injecting layer/a cathode;
(4) An anode/a hole injecting layer/a light emitting layer/an electron injecting layer/a cathode;
(5) An anode/an organic semiconductor layer/a light emitting layer/a cathode;
(6) An anode/an organic semiconductor layer/an electron barrier layer/a light emitting layer/a cathode;
(7) An anode/an organic semiconductor layer/a light emitting layer/an adhesion improving layer/a cathode;
(8) An anode/a hole injecting layer/a hole transporting layer/a light emitting layer/an electron injecting layer/a cathode;

(9) An anode/an insulating layer/a light emitting layer/an insulating layer/a cathode;
(10) An anode/an inorganic semiconductor layer/an insulating layer/a light emitting layer/an insulating layer/a cathode;
(11) An anode/an organic semiconductor layer/an insulating layer/a light emitting layer/an insulating layer/a cathode;
(12) An anode/an insulating layer/a hole injecting layer/a hole transporting layer/a light emitting layer/an insulating layer/a cathode; and
(13) An anode/an insulating layer/a hole injecting layer/a hole transporting layer/a light emitting layer/an electron injecting layer/a cathode.

Among the above constructions, construction (8) is preferable. However, the construction of the organic EL device is not limited to those shown above as the examples. The aromatic compound of the present invention may be used in any of the above organic layers. Among the above constructions, the constructions using the aromatic compound of the present invention in the light emitting zone or the hole transporting zone are preferable.

EXAMPLES

The present invention will be described more specifically with reference to examples in the following. However, the present invention is not limited to the examples.

Synthesis Example 1

Synthesis of 9-(naphthyl-2-yl) 10-(4-(naphthyl-1-yl) phenyl-1-yl)anthracene (BH1)

(1) Synthesis of 9-(naphthyl-2-yl)anthracene

Under the stream of nitrogen, 30.0 kg of 9-bromoanthracene (manufactured by Tokyo Chemical Industry Co., Ltd.), 24.1 kg of 2-naphthylboronic acid, 2.157 kg of tetrakis (triphenylphosphine)palladium, 48.4 kg of potassium carbonate (manufactured by NIPPON SODA Co., Ltd.), 150 liters of toluene and 150 liters of Solmix were placed into a 1,000 liter reactor, and the reaction was allowed to proceed at 78° C. for 50 hours.

After the reaction mixture was cooled to the room temperature, 188 liters of tetrahydrofuran and 188 liters of water were added, and the obtained mixture was fractionated. The obtained organic layer was washed with 115 liters of a 5% by mass aqueous solution of sodium hydroxide, 115 liters of a 5% by mass aqueous solution of sodium hydrogencarbonate and 115 liters of a 5% by mass aqueous solution of sodium chloride, successively, and the washed organic layer was concentrated under a reduced pressure.

The organic layer was purified using a column packed with 300 kg of silica gel and toluene as the developing solvent and concentrated under a reduced pressure. Then, 590 liters of heptane was added until a slurry was obtained, and the obtained slurry was filtered at the room temperature. The obtained residue was dried, and 33.2 kg of 9-(naphthyl-2-yl) anthracene was obtained.

(2) Synthesis of 9-bromo-10-(naphthyl-2-yl)anthracene

Under the stream of nitrogen, 33.2 kg of 9-(naphthyl-2-yl)-anthracene obtained above in (1) and 265 liters of dimethylformamide were placed into a 1,000 liter reactor, and a solution obtained by dissolving 21.36 kg of N-bromosuccimide (manufactured by MIDORI KAGAKU Co., Ltd.) in 100 liters of dimethylformamide was added dropwise at a temperature in the range of 30 to 35° C.

After the reaction was allowed to proceed for 4 hours, 454 liters of water was added dropwise. The obtained reaction product was filtered, and the obtained crystals were washed with 60 liters of water. The washed crystals were dissolved into 276 liters of chloroform, and the resultant solution was washed with 80 liters of water and dried with 7 kg of magnesium sulfate. The organic layer was concentrated under a reduced pressure, and 590 liters of n-heptane was added until a slurry was obtained. The slurry was filtered at the room temperature, and the obtained crystals were dissolved into 57 liters of toluene. After 230 liters of n-heptane was added, the resultant mixture was cooled to −5° C. The temperature was then elevated to 60° C., and the crystals were separated by filtration. The separated crystals were dried, and 34.6 kg of 9-bromo-10-(naphthyl-2-yl)anthracene was obtained.

(3) Synthesis of (9-(naphthyl-2-yl)anthracene-10-yl)boronic acid

Under the stream of nitrogen, 17.3 kg of 9-bromo-10-(naphthyl-2-yl)anthracene obtained above in (2) and 138 liters of tetrahydrofuran were placed into a 200 liter reactor. The mixture was cooled at −70° C., and 20.4 kg of a 17% by mass hexane solution of n-butyllithium (manufactured by ASIA LITHIUM Co. Ltd.) was added dropwise at a temperature in the range of −64 to −70° C., and the reaction was allowed to proceed at the same temperature for 2 hours. To the obtained reaction mixture, 9.38 kg of trimethyl borate (manufactured by Daihachi Chemical Industry Co., Ltd.) was added dropwise at a temperature in the range of −64 to −70° C., and the reaction was allowed to proceed at the same temperature for 2 hours. To the obtained reaction mixture, 103 liters of a 5 moles/liter hydrochloric acid was added dropwise at a temperature of 5° C. or lower. The obtained product was fractionated at the room temperature, and the organic layer was washed with 60 liters of a 5% by mass solution of sodium hydrogencarbonate and treated by extraction with 60 liters of toluene.

The step having the same procedures as those described above was conducted once more, and the products in the two steps were combined. The combined product was washed with 120 liters of a 10% by mass aqueous solution of sodium chloride and concentrated under a reduced pressure. To the concentrated product, 200 liters of n-heptane was added until a slurry was obtained. The crystals in the slurry were separated by filtration, washed in 30 liters of toluene heated at 50° C., cooled to the room temperature, separated by filtration and dried, and 20.3 kg of (9-(naphthyl-2-yl)anthracene-10-yl)boronic acid was obtained.

(4) Synthesis of 1-(4-bromophenyl-1-yl)naphthalene

Under the stream of nitrogen, 14.7 kg of 1-naphthylboronic acid, 22.0 kg of 4-bromoiodobenzene, 1.797 kg of tetrakis (triphenylphosphine)-palladium, 24.7 kg of potassium carbonate (manufactured by NIPPON SODA Co., Ltd.) and 220 liters of toluene were placed into a reactor having an inner volume of 500 liters, and the reaction was allowed to proceed at 75° C. for 32 hours.

To the obtained reaction mixture, 220 liters of water was added, and the resultant product was fractionated. The obtained organic layer was washed with 130 liters of a 5% by mass aqueous solution of sodium hydroxide, 130 liters of a 5% by mass aqueous solution of sodium hydrogencarbonate and 130 liters of a 5% by mass aqueous solution of sodium chloride, successively. The washed product was concentrated under a reduced pressure and purified using a column packed with 220 kg of silica gel and n-heptane as the developing solvent. After the purified product was concentrated under a reduced pressure and distilled under a reduced pressure, 16.9 kg of 1-(4-bromophenyl-1-yl)naphthalene was obtained.

(5) Synthesis of 9 (naphthyl-2-yl)-10-(4-(naphthyl-1-yl)phenyl-1-yl)-anthracene (BH1)

Under the stream of nitrogen, 5.0 kg of (9-(naphthyl-2-yl)-anthracene-10-yl)boronic acid obtained above in (3), 4.07 kg of 1-(4-bromophenyl-1-yl)naphthalene obtained above in (4), 332 g of tetrakis(triphenylphosphine)palladium, 5.95 kg of potassium carbonate (manufactured by NIPPON SODA Co., Ltd.), 50 liters of water and 50 liters of dimethoxyethane were placed into a reactor having an inner volume of 200 liters, and the reaction was allowed to proceed at 75° C. for 18 hours.

After the reaction mixture was cooled to the room temperature, the crystals were separated by filtration and washed with 24 liters of water, 24 liters of methanol and 24 liters of n-heptane and then in 44 liters of n-heptane heated at 50° C. After being cooled to the room temperature, the crystals were separated by filtration.

The obtained crystals were purified using a column packed with 25 kg of silica gel and a mixed solvent of hexane and toluene (hexane/toluene=3/1), concentrated under a reduced pressure, filtered after adding 2.5 liters of acetone and washed with 2.5 liters of acetone and 2.5 liters of hexane. After the washed product was dried, the product was purified by sublimation under the condition of a degree of vacuum of $3 \times 10^{-3}$ Pa and a temperature of the boat of 270 to 280° C., and 4.81 kg of 9-(naphthyl-2-yl)-10-(4-(naphthyl-1-yl)phenyl-1-yl) anthracene (BH1) was obtained.

The purity of BH1 obtained above measured in accordance with the high performance liquid chromatography (HPLC) was 99.98% as the ratio of BH1 peak area to all peak area. When the content of bromine present in BH1 was measured in accordance with the ICP-MS (burning) method, the content was found to be 28 ppm by mass.

Example 1

Treatment of BH1 by the Grignard Reaction

Under the stream of argon, 600 g of BH1 was suspended in 9 liters of anhydrous tetrahydrofuran (THF). To the resultant suspension, 60 ml of a 32% by mass tetrahydrofuran solution of phenylmagnesium bromide (manufactured by Tokyo Chemical Industry Co., Ltd.) was slowly added dropwise under cooling with ice, and the obtained mixture was stirred at 50 to 60° C. for 30 minutes. To the obtained mixture, a dilute sulfuric acid was added to decompose the unreacted substances. The reaction product was treated by extraction with toluene, and the organic layer was washed with a 5% by mass aqueous solution of NaOH, a 5% by mass aqueous solution of sodium hydrogencarbonate and a 10% by mass aqueous solution of sodium chloride and concentrated under a reduced pressure. Toluene was added to the residue of the concentration to form a material fluid. The material fluid was purified using a column packed with silica gel and alumina, and the obtained fluid was concentrated under a reduced pressure. When a slurry was obtained, 2 liters of heptane was slowly added, and the resultant mixture was cooled. After being cooled to 5° C., the crystals were separated by filtration, and 490 g of yellow crystals were obtained.

The obtained yellow crystals were purified by sublimation under the condition of a degree of vacuum of $3 \times 10^{-3}$ Pa and a temperature of the boat of 270 to 280° C., and 415 g of BH1 treated by the Grignard reaction (referred to as GBH1, hereinafter) was obtained.

The purity of GBH1 obtained above measured in accordance with HPLC was 99.99% or greater as the ratio of GBH1 peak area to all peak area. When the content of bromine present in GBH1 was measured in accordance with the ICP-MS (burning) method, the content was found to be smaller than 1 ppm by mass.

Example 2

Treatment of BH1 by the Reaction with an Organolithium Reagent

Under purging with nitrogen, 600 g of BH1 was dissolved into 5 liters of anhydrous toluene and 5 liters of anhydrous ether. To the obtained solution, 75 ml of a 15% by mass hexane solution of n-butyllithium (manufactured by Tokyo Chemical Industry Co., Ltd.) was slowly added at −78° C. The reaction mixture was stirred at 0° C. for 1 hour, and then the reaction was stopped by adding water. The reaction product was treated by extraction with toluene. The organic layer was washed with a 5% by mass aqueous solution of NaOH, a 5% by mass aqueous solution of sodium hydrogencarbonate and a 10% by mass aqueous solution of sodium chloride and then concentrated under a reduced pressure. Toluene was added to the residue of the concentration to form a material fluid. The material fluid was purified using a column packed with silica gel and alumina, and the obtained fluid was concentrated under a reduced pressure. When a slurry was obtained, 2 liters of heptane was slowly added, and the resultant mixture was cooled. After being cooled to 5° C., the crystals were separated by filtration, and 495 g of yellow crystals were obtained.

The obtained yellow crystals were purified by sublimation under the condition of a degree of vacuum of $3 \times 10^{-3}$ Pa and a temperature of the boat of 270 to 280° C., and 421 g of BH1 treated by the reaction with an organolithium reagent (referred to as LBH1, hereinafter) was obtained.

The purity of LBH1 obtained above measured in accordance with HPLC was 99.99% or greater as the ratio of LBH1 peak area to all peak area. When the content of bromine present in LBH1 was measured in accordance with the ICP-MS (burning) method, the content was found to be smaller than 1 ppm by mass.

Example 3

Treatment of BH1 by the Suzuki Coupling Reaction

Under purging with nitrogen, 600 g of BH1, 9 liters of toluene, 14.4 g of phenylboronic acid, 49.2 g of potassium carbonate, 3 liters of water and 26 g of Pd(PPh$_3$)$_4$ were placed into a reactor, and the temperature was elevated to 75° C. After the reaction mixture was aged at the same temperature for one night, the aqueous layer was removed. The organic layer was washed with a 5% by mass aqueous solution of NaOH, a 5% by mass aqueous solution of sodium hydrogencarbonate and a 10% by mass aqueous solution of sodium chloride and then concentrated under a reduced pressure. Toluene was added to the residue of the concentration to form a material fluid. The material fluid was purified using a column packed with silica gel and alumina, and the obtained fluid was concentrated under a reduced pressure. When a slurry was obtained, 1,920 ml of heptane was slowly added, and the resultant mixture was cooled. After being cooled to 5° C., the crystals were separated by filtration, and 540 g of yellow crystals were obtained.

The obtained yellow crystals were purified by sublimation under the condition of a degree of vacuum of $3 \times 10^{-3}$ Pa and a temperature of the boat of 270 to 280° C., and 475 g of BH1 treated by the Suzuki reaction (referred to as SBH1, hereinafter) was obtained.

The purity of SBH1 obtained above measured in accordance with HPLC was 99.99% or greater as the ratio of SBH1 peak area to all peak area. When the content of bromine present in SBH1 was measured in accordance with the ICP-MS (burning) method, the content was found to be smaller than 1 ppm by mass.

Synthesis Example 2

Synthesis of N,N,N',N'-tetra(4-biphenylyl)-benzidine (HT1)

Into a three-necked flask having an inner volume of 1,000 ml, 100 g of 4-bromobiphenyl (manufactured by Tokyo Chemical Industry Co., Ltd.), 23.1 g of benzamide (manufactured by Tokyo Chemical Industry Co., Ltd.), 3.6 g of cuprous iodide (manufactured by Kanto Chemical Co., Inc.) and 58 g of anhydrous potassium carbonate (manufactured by Kanto Chemical Co., Inc.) were placed. Then, a stirrer was placed into the flask, and rubber caps were set at the two side inlets. A curled tube condenser for refluxing was set at the central inlet of the flask. A three-way stopcock was set above the condenser, and a balloon filled with argon gas was set above the three-way stopcock. The system was purged with the argon gas in the balloon three times using a vacuum pump.

Then, 500 ml of diethylbenzene was added by a syringe through a rubber septum. The flask was set in an oil bath, and the temperature was slowly elevated to 200° C. while the solution was stirred. After 6 hours, the flask was removed from the oil bath to complete the reaction and left standing for 12 hours under the atmosphere of argon.

The reaction solution was transferred to a separation funnel, and 1,000 ml of dichloromethane was added to dissolve precipitates. The organic layer was washed with 600 ml of a saturated aqueous solution of sodium chloride and dried with anhydrous potassium carbonate. Potassium carbonate was removed from the organic layer by filtration, and the solvent in the obtained organic layer was removed by distillation. To the obtained residue, 2,000 ml of toluene and 400 ml of ethanol were added. After attaching a drying tube, the mixture was heated at 80° C., and the residue was completely dissolved. After being left standing for 12 hours, the solution was slowly cooled to the room temperature so that recrystallization could be achieved.

The obtained crystals were separated by filtration and dried in vacuum at 60° C., and 74 g of N,N-di-(4-biphenylyl)benzamide was obtained.

Into a three-necked flask having an inner volume of 3 liters, 70 g of N,N-di-(4-biphenylyl)benzamide, 31.5 g of 4,4'-diiodobiphenyl (manufactured by Wako Pure Chemical Industries Ltd.), 1.5 g of cuprous iodide and 36 g of potassium hydroxide were placed. A rubber cap was attached to one of the side inlets. A curled tube condenser for refluxing was set at the central inlet of the flask. A three-way stopcock was set above the condenser, and a balloon filled with argon gas was set above the three-way stopcock. The system was purged with the argon gas in the balloon three times using a vacuum pump.

Then, 1,000 ml of xylene was added by a syringe through a rubber septum. The flask was set in an oil bath, and the temperature was slowly elevated to 140° C. while the solution was stirred. After stirring at 140° C. for 6 hours, the flask was removed from the oil bath and left standing for 12 hours.

After the formed precipitates were completely dissolved by adding 3 liters of dichloromethane, the resultant solution was transferred to a separation funnel. After washing with 3 liters of a saturated aqueous solution of sodium chloride, the separated organic layer was dried with anhydrous potassium carbonate. After filtration, the solvent was removed by distillation. To the obtained residue, 10 liters of toluene and 3 liters of ethanol were added. After a drying tube was attached, the mixture was heated at 80° C., and the residue was completely dissolved. The resultant solution was slowly cooled to the room temperature. Then, the precipitates were separated by filtration, washed with small amounts of toluene and ethanol, dried in a vacuum dryer at 60° C. for 3 hours and purified by sublimation under the condition of a degree of vacuum of $3 \times 10^{-3}$ Pa and a temperature of the boat of 360 to 370° C., and 70 g of N,N,N',N'-tetra(4-biphenylyl)benzidine (HT1) was obtained.

The purity of HT1 obtained above measured in accordance with HPLC was 99.98% as the ratio of HT1 peak area to all peak area. When the content of bromine present in HT1 was measured in accordance with the ICP-MS (burning) method, the content was found to be 20 ppm by mass.

Example 4

Treatment of HT1 by Chemical Reaction

Under purging with nitrogen, 50 g of HT1, 5 liters of toluene, 0.8 g of phenylboronic acid, 2.7 g of potassium carbonate and 1.4 g of $Pd(PPh_3)_4$ were placed into a reactor, and the temperature was elevated to 75° C. After the reaction mixture was aged at the same temperature for one night, the reaction mixture was cooled, and the aqueous layer was removed. The precipitates were separated by filtration, washed with water, methanol and acetone and purified by recrystallization using toluene, and 47 g of yellow crystals were obtained.

The obtained yellow crystals were purified by sublimation under the condition of a degree of vacuum of $3 \times 10^{-3}$ Pa and a temperature of the boat of 350 to 360° C., and 41 g of HT1 treated by chemical reaction (referred to as SHT1, hereinafter) was obtained.

The purity of SHT1 obtained above measured in accordance with HPLC was 99.99% or greater as the ratio of STH1 peak area to all peak area. When the content of bromine present in SHT1 was measured in accordance with the ICP-MS (burning) method, the content was found to be smaller than 1 ppm by mass.

Example 5

Evaluation of GBH1

A glass substrate having a size of 25 mm×75 mm×1.1 mm thickness and an ITO transparent electrode (manufactured by GEOMATEC Company) was cleaned by application of ultrasonic wave in isopropyl alcohol for 5 minutes and then by exposure to ozone generated by ultraviolet light for 30 minutes.

The cleaned glass substrate having the transparent electrode was attached to a substrate holder of a vacuum vapor deposition apparatus. On the surface of the cleaned substrate at the side having the transparent electrode, a film of HT1 having a thickness of 80 nm was formed in a manner such that the formed film covered the transparent electrode. The formed film of HT1 worked as the hole transporting layer.

Then, a film of GBH1 having a thickness of 40 nm was formed by vapor deposition. At the same time, an amine compound D1 expressed by the formula shown in the following was vapor deposited in an amount such that the ratio of the amounts by mass of GBH1 to D1 was 40:2. The formed film worked as the light emitting layer.

On the formed film, a film of Alq (tris(8-hydroxyquinoline)-aluminum expressed by the formula shown in the following) having a thickness of 20 nm was formed. The film of Alq worked as the electron transporting layer. Thereafter, LiF was vapor deposited to form a film having a thickness of 1 nm so that an electron injecting layer was formed. Metallic Al was vapor deposited on the formed film of LiF to form a metal cathode, and an organic EL device was obtained. The color of the light emitted from the organic EL device was blue.

The result of the measurement of the half lifetime of the light emission when the device was driven under a constant DC current at an initial luminance of 5,000 nit at the room temperature is shown in Table 1.

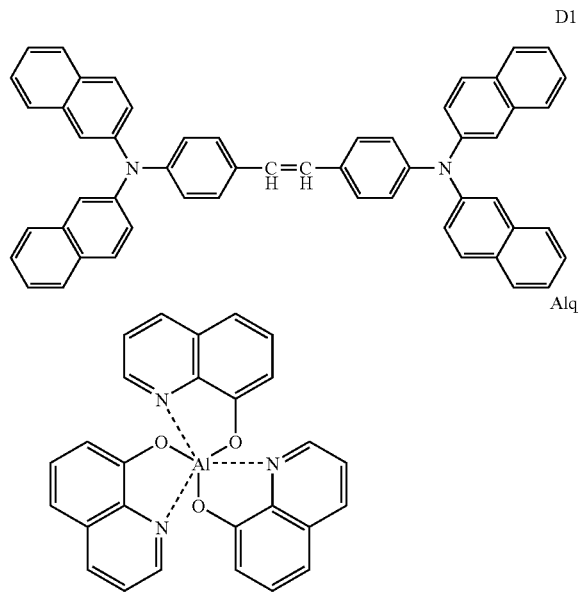

Example 6

Evaluation of LBH1

An organic EL device was prepared in accordance with the same procedures as those conducted in Example 5 except that LBH1 was used in place of GBH1. The prepared organic EL device emitted blue light. The result of the measurement of the half lifetime of the light emission when the device was driven under a constant DC current at an initial luminance of 5,000 nit at the room temperature is shown in Table 1.

Example 7

Evaluation of SBH1

An organic EL device was prepared in accordance with the same procedures as those conducted in Example 5 except that SBH1 was used in place of GBH1. The prepared organic EL device emitted blue light. The result of the measurement of the half lifetime of the light emission when the device was driven under a constant DC current at an initial luminance of 5,000 nit at the room temperature is shown in Table 1.

Example 8

Evaluation of SHT1

An organic EL device was prepared in accordance with the same procedures as those conducted in Example 5 except that SHT1 was used in place of HT1, and BH1 was used in place of GBH1. The prepared organic EL device emitted blue light. The result of the measurement of the half lifetime of the light emission when the device was driven under a constant DC current at an initial luminance of 5,000 nit at the room temperature is shown in Table 1.

Example 9

Evaluation of GBH1 and SHT1

An organic EL device was prepared in accordance with the same procedures as those conducted in Example 5 except that SHT1 was used in place of HT1. The prepared organic EL device emitted blue light. The result of the measurement of the half lifetime of the light emission when the device was driven under a constant DC current at an initial luminance of 5,000 nit at the room temperature is shown in Table 1.

Comparative Example 1

An organic EL device was prepared in accordance with the same procedures as those conducted in Example 5 except that BH1 was used in place of GBH1. The prepared organic EL device emitted blue light. The result of the measurement of the half lifetime of the light emission when the device was driven under a constant DC current at an initial luminance of 5,000 nit AT the room temperature is shown in Table 1.

TABLE 1

|  | Hole transporting layer content of Br (ppm by mass) | Light emitting layer (host material) content of Br (ppm by mass) | Half lifetime, initial luminance 5,000 nit (h) |
| --- | --- | --- | --- |
| Example 5 | HT1 28 | GBH1 <1 | 450 |
| Example 6 | HT1 28 | LBH1 <1 | 440 |
| Example 7 | HT1 28 | SBH1 <1 | 440 |
| Example 8 | SHT1 <1 | BH1 20 | 460 |
| Example 9 | SHT1 <1 | GBH1 <1 | 590 |
| Comparative Example 1 | HT1 28 | BH1 20 | 280 |

It is shown by the above results that the half lifetime was remarkably improved when the material obtained by the dehalogenation treatment using chemical reaction was used for the organic EL device. In particular, the effect was more remarkable when the materials obtained by the dehalogenation treatment were used for both of the hole transporting layer and the light emitting layer.

Synthesis Example 3

Synthesis of 2-(2-biphenylyl)-9,10-bis(3-(1-naphthyl)phenyl)anthracene (BH2)

BH2 expressed by the following formula (A) was synthesized in accordance with the following route of synthesis:

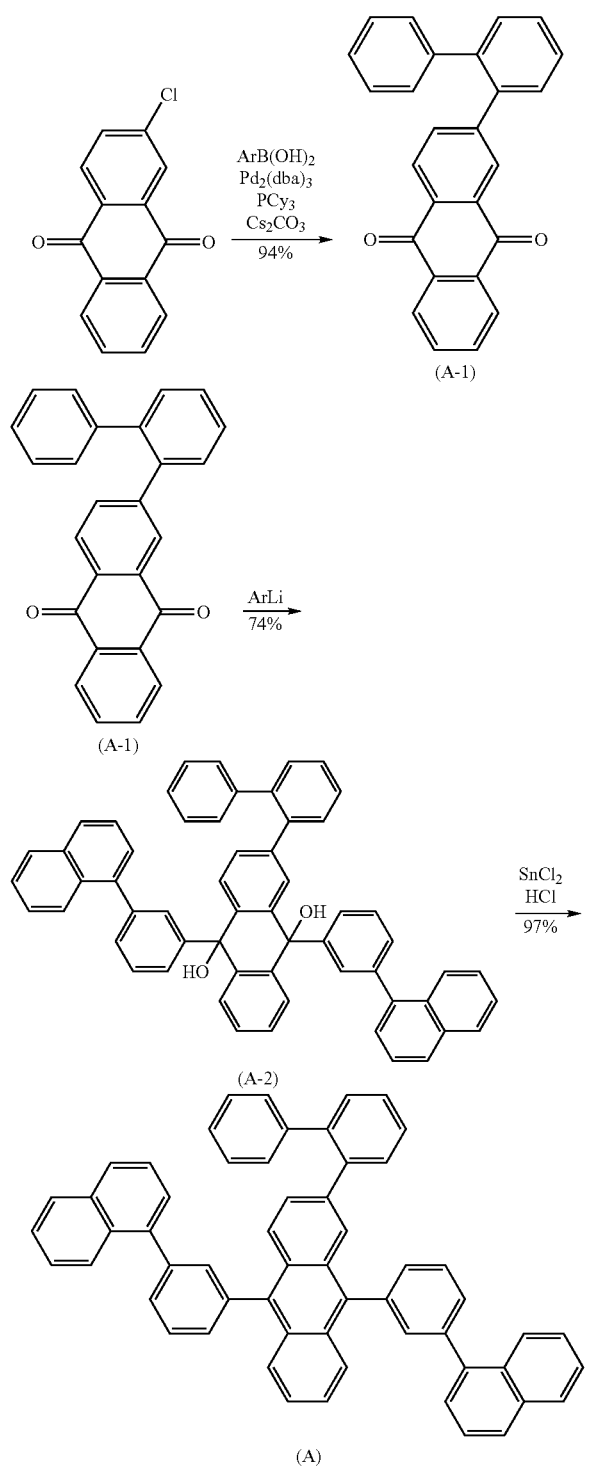

(1) Synthesis of 2-biphenylyl-9,10-anthraquinone [Compound (A-1)]

Under the atmosphere of argon, 3.4 g (14 mmole) of 2-chloro-anthraquinone, 5 g (17 mmole, 1.2 eq) of 2-biphenylylboronic acid, 0.32 g (0.35 mmole; 5% by mass Pd) of tris(dibenzylideneacetone)dipalladium(0) and 14 g (43 mmole; 2.5 eq) of cesium carbonate were suspended in 40 ml of anhydrous dioxane. Then, 1.1 ml (25% by mass; 0.98 mmole; 1.4 eq to Pd) of a toluene solution of tricyclohexylphosphine was added, and the resultant mixture was stirred at 80° C. for 10 hours.

The obtained reaction mixture was diluted with 100 ml of water and 300 ml of toluene, and insoluble components were removed by filtration with zeolite. The organic layer was separated from the filtrate, washed with 50 ml of a saturated aqueous solution of sodium chloride and dried with anhydrous magnesium sulfate. The solvent was removed by distillation, and a deep red oily substance was obtained. The obtained oily substance was purified in accordance with the column chromatography (the column packed with silica gel). The purification was conducted with a mixed solvent of hexane and 33% by mass of dichloromethane and then with a mixed solvent of hexane and 50% by mass of dichloromethane. After the purification, 7.1 g (the yield: 94%) of a light yellow solid substance was obtained. The obtained solid substance was identified to be Compound (A-1) described above in accordance with $^1$H-NMR and the field desorption mass analysis (FDMS). The results of the measurements of $^1$H-NMR and FDMS are shown in the following.

$^1$H-NMR (CDCl$_3$, TMS) δ: 7.18 (5H, s), 7.49 (5H, s), 7.76 (2H, dd, J=6 Hz, 3 Hz), 8.08 (1H, d, J=8 Hz), 8.2-8.3 (3H, m)

FDMS calcd. for C$_{26}$H$_{16}$O$_2$=360; found: m/z=360 (M$^+$, 100)

(2) Synthesis of 2-(2-biphenylyl)-9,10-bis(3-(1-naphthyl)phenyl)-9,10-dihydroxy-9,10-dihydroanthracene [Compound (A-2)]

Under the atmosphere of argon, 4.2 g (15 mmole, 2.7 eq) of 3-(1-naphthyl)-1-bromobenzene was dissolved into 25 ml of anhydrous toluene and 25 ml of anhydrous THF, and the resultant solution was cooled at −20° C. in a dry ice/methanol bath. To the cooled solution, 10 ml (1.59 moles/liter, 15.9 mmole, 1.06 eq) of a hexane solution of n-butyl-lithium was added, and the obtained mixture was stirred at −20° C. for 1 hour. To the resultant mixture, 2.0 g (5.6 mmole) of 2-(2-biphenylyl)-9,10-anthraquinone [Compound (A-1)] was added. The resultant mixture was stirred at the room temperature for 2 hours and left standing at the room temperature for one night.

The obtained reaction mixture was deactivated with 50 ml of a saturated aqueous solution of ammonium chloride. The organic layer was separated, washed with 50 ml of a saturated aqueous solution of sodium chloride and dried with magnesium sulfate. After the solvent was removed by distillation, a yellow oily substance was obtained. The oily substance was purified in accordance with the column chromatography (the column packed with silica gel). In the purification, the elution was conducted with a mixed solvent of hexane and 50% by mass of dichloromethane, then with dichloromethane and with a mixed solvent of dichloromethane and 3% by mass of methanol. After the purification, 3.1 g (the yield: 74%) of a light yellow amorphous solid compound was obtained. The obtained solid compound was identified to be Compound (A-2) described above in accordance with $^1$H-NMR. The result of the measurements of $^1$H-NMR is shown in the following.

$^1$H-NMR (CDCl$_3$, TMS) δ: 2.36 (1H, s), 2.89 (1H, s), 6.7-7.9 (38H, m)

(3) Synthesis of 2-(2-biphenylyl)-9,10-bis(3-(1-naphthyl)phenyl)-anthracene (BH2)

Into 25 ml of THF, 1.1 g (1.4 mmole) of 2-(2-biphenylyl)-9,10-bis(3-(1-naphthyl)phenyl)-9,10-dihydroxy-9,10-dihydroanthracene [Compound (A-2)] and 6.5 g (29 mmole, 20 eq) of stannic chloride dihydrate were suspended. After 15 ml of a concentrated hydrochloric acid was added, the resultant mixture was heated under the refluxing condition for 10 hours.

The obtained reaction mixture was separated by filtration, washed with water and methanol, successively, and dried, and a light yellow solid substance was obtained. The obtained solid substance was purified in accordance with the column chromatography (the column packed with silica gel). In the purification, the elution was conducted with a mixed solvent of hexane and 20% by mass of dichloromethane. After the purification, 1.0 g (the yield: 97%) of a light yellow solid substance was obtained. The obtained solid substance was identified to be BH2 described above in accordance with $^1$H-NMR and FDMS. The results of the measurements of $^1$H-NMR and FDMS are shown in the following. The contents of halogen elements in BH2 were measured in accordance with the ICP-MS (burning) method and found to be as follows: the content of I: 5 ppm by mass; the content of Br: 21 ppm by mass; and the content of Cl: 41 ppm by mass.

$^1$H-NMR (CDCl$_3$, TMS) δ: 6.93 (5H, bs), 7.2-7.9 (31H, m), 8.0-8.1(2H, m) FDMS calcd. for C$_{58}$H$_{38}$=734; found: m/z=734 (M+, 100) λmax: 407, 385, 366 nm (PhMe) Fmax: 426, 446 nm (PhMe, λex=405 nm) Ip=5.69 eV (500 nW, 82Y/eV) Eg=2.92 eV Tg=130° C.

Example 10

Treatment of BH2 by Chemical Reaction with an Organolithium Reagent

Under the atmosphere of argon, 2.0 g of BH2 was dissolved into a mixed solvent of 10 ml of anhydrous THF and 10 ml of toluene, and the obtained solution was cooled at −30° C. To the cooled solution, 1.0 ml of a 1.6 moles/liter hexane solution of n-butyllithium was slowly added, and the resultant mixture was stirred at −30° C. for 5 hours. After 1.0 ml of water was slowly added to the reaction fluid, the obtained mixture was concentrated by an evaporator under a reduced pressure. The obtained solid substance was washed with methanol and dried under a reduced pressured. The residue was purified in accordance with the column chromatography (the column packed with silica gel). In the purification, the elution was conducted with a mixed solvent of hexane and toluene (hexane/toluene=3/1 (the ratio of the amounts by mass)). The obtained solid substance was washed with methanol and dried under a reduced pressure, and 1.6 g (the recovery: 80%) of a yellow solid substance was obtained. The obtained solid substance will be referred to as LBH2.

The contents of halogen elements in the solid substance were measured in accordance with the ICP-MS (burning) method, and it was found that the contents of I, Br and Cl were all smaller than 5 ppm by mass.

Example 11

Treatment of BH2 by Chemical Reaction

Under the atmosphere of argon, 2.0 g of BH2, 40 mg (0.1 eq of BH2) of phenylboronic acid and 10 mg (0.03 eq of phenylboronic acid) of tetrakis(triphenylphosphino)palladium(0) were dissolved into 10 ml of anhydrous toluene, and the resultant solution was cooled at −30° C. To the cooled solution, 1.3 ml of a 2 moles/liter aqueous solution of sodium carbonate was added, and the resultant mixture was stirred at 80° C. for 6 hours. After 1.0 ml of water was slowly added to the obtained reaction fluid, the resultant mixture was concentrated by an evaporator under a reduced pressure. The obtained solid substance was washed with methanol and dried under a reduced pressure. The residue was purified in accordance with the column chromatography (the column packed with silica gel). In the purification, the elution was conducted with toluene and then with methylene chloride. The obtained solid substance was washed with methanol and dried under a reduced pressure, and 2.0 g (the recovery: 100%) of a yellow solid substance was obtained. The obtained solid substance will be referred to as SBH2.

The contents of halogen elements in the solid substance were measured in accordance with the ICP-MS (burning) method, and it was found that the contents of I, Br and Cl were all smaller than 5 ppm by mass.

Example 12

Evaluation of LBH2

A glass substrate having a size of 25 mm×75 mm×1.1 mm thickness and an ITO transparent electrode (manufactured by GEOMATEC Company) was cleaned by application of ultrasonic wave in isopropyl alcohol for 5 minutes and then by exposure to ozone generated by ultraviolet light for 30 minutes.

The cleaned glass substrate having the transparent electrode was attached to a substrate holder of a vacuum vapor deposition apparatus. On the surface having the transparent electrode, a film of N,N'-bis(4-diphenylaminophenyl) N,N'-diphenyl-4,4'-diaminobiphenyl (TPD232) having a thickness of 40 nm was formed in a manner such that the formed film covered the transparent electrode. The formed film of TPD232 worked as the hole injecting layer.

On the film of TPD232, a film of N,N,N',N'-tetrakis(4-biphenyl)-4,4'-benzidine (BPTPD) having a thickness of 40 nm was formed by vapor deposition. The film of BPTPD worked as the hole transporting layer.

LBH2 and 1,6-bis(diphenylamino)pyrene in amounts such that the ratio of the amounts by mass was 20:1 were dissolved into a mixed solvent of dioxane and isopropyl alcohol (1:8 as the ratio of the amounts by volume), and a 3% by mass coating solution was prepared. Using the prepared coating solution, a light emitting layer having a thickness of 40 nm was formed on the film of BPTPD in accordance with the spin coating process. The obtained laminated substrate was heated by an infrared heat source (a halogen lamp) under a vacuum of about 10$^{-6}$ Pa so that the temperature of the substrate was elevated at 120° C.

It was confirmed from the result of the measurement by the quadrupole mass spectrometer that the residual solvents in the films could be removed by the heating for 30 minutes. Thereafter, the laminated substrate was transferred to the inside of the vacuum vapor deposition apparatus by an apparatus for transfer of the substrate while the laminated substrate was kept without contacting the outside atmosphere. A film of Alq (tris(8-hydroxyquinoline)aluminum, expressed by the formula shown above) having a thickness of 30 nm was formed in accordance with the vacuum vapor deposition process. The film of Alq worked as the electron transporting layer.

Then, a film of lithium fluoride having a thickness of 1 μm was formed in accordance with the vacuum vapor deposition process as the electron injecting layer. On the electron injecting layer, metallic aluminum was vapor deposited to form a metal cathode, and an organic EL device was prepared. When a voltage of 5.0 V was applied to the device, an electric current of 2.3 mA/cm² passed, and blue light having chromaticity coordinates of (0.15, 0.26) was emitted at a luminance of 94 cd/m². The current efficiency was 4.1 cd/A and 2.61 m/W. When the device was driven at the room temperature with a small electric current at an initial luminance of 100 cd/m², the half lifetime of the luminance was 13,000 hours.

Example 13

Evaluation of SBH2

An organic EL device was prepared in accordance with the same procedures as those conducted in Example 12 except that SBH2 was used in place of LBH2. When a voltage of 5.0 V was applied to the device, an electric current of 2.3 mA/cm² passed, and blue light having chromaticity coordinates of (0.15, 0.26) was emitted at a luminance of 92 cd/m². The current efficiency was 4.0 cd/A and 2.51 m/W. When the device was driven at the room temperature with a small electric current at an initial luminance of 100 cd/m², the half lifetime of the luminance was 12,000 hours.

Comparative Example 2

Evaluation of BH2

An organic EL device was prepared in accordance with the same procedures as those conducted in Example 12 except that BH2 was used in place of LBH2. When a voltage of 5.0 V was applied to the device, an electric current of 2.5 mA/cm² passed, and blue light having chromaticity coordinates of (0.15, 0.26) was emitted at a luminance of 93 cd/m². The current efficiency was 3.7 cd/A and 2.31 m/W. When the device was driven at the room temperature with a small electric current at an initial luminance of 100 cd/m², the half lifetime of the luminance was 9,800 hours.

INDUSTRIAL APPLICABILITY

The aromatic compound obtained in accordance with the process of the present invention can be advantageously used as the material for organic EL devices, organic semiconductors and electronic photosensitive substances.

The invention claimed is:

1. A process for producing an aromatic compound, comprising:
   bringing an aromatic compound into reaction with a dehalogenating agent to decrease the contents of halogen elements to 10 ppm by mass or smaller;
   wherein:
   the aromatic compound is produced via an intermediate compound comprising at least one halogen element; and
   a content of the at least one halogen element in the aromatic compound is from 10 to 1,000 ppm by mass.

2. A process for producing an aromatic compound according to claim 1, wherein the aromatic compound is an organic material for electroluminescence.

3. A process for producing an aromatic compound according to claim 1, wherein the dehalogenating agent is at least one agent selected from Grignard reagents, organolithium compounds and boronic acid derivatives.

4. A process for producing an aromatic compound according to claim 1, wherein the aromatic compound is a compound having a condensed aromatic ring having 14 to 20 ring carbon atoms in a molecule.

5. A process for producing an aromatic compound according to claim 1, wherein the aromatic compound is a compound having 1 to 12 nitrogen atoms in a molecule.

6. A process for producing an aromatic compound according to claim 1, wherein the halogen element is at least one element selected from bromine and iodine.

7. A process for producing an aromatic compound according to claim 3, wherein the Grignard reagent is at least one reagent selected from phenylmagnesium bromide, phenylmagnesium iodide, ethylmagnesium bromide and ethylmagnesium iodide.

8. A process for producing an aromatic compound according to claim 3, wherein the organolithium compound is at least one compound selected from n-butyllithium and phenyllithium.

9. A process for producing an aromatic compound according to claim 3, wherein the boronic acid derivative is phenylboronic acid.

* * * * *